United States Patent [19]
Kaali

[11] Patent Number: 5,720,761
[45] Date of Patent: Feb. 24, 1998

[54] VISUALLY DIRECTED TROCAR AND METHOD

[75] Inventor: Steven G. Kaali, Dobbs Ferry, N.Y.

[73] Assignee: Worldwide Optical Trocar Licensing Corp., Dobbs Ferry, N.Y.

[21] Appl. No.: 648,082

[22] PCT Filed: Jul. 29, 1994

[86] PCT No.: PCT/US94/08683

§ 371 Date: May 10, 1996

§ 102(e) Date: May 10, 1996

[87] PCT Pub. No.: WO95/13751

PCT Pub. Date: May 26, 1995

[51] Int. Cl.⁶ .......................... A61B 17/34; A61M 5/00
[52] U.S. Cl. .......................... 606/185; 600/101; 604/264
[58] Field of Search ........................ 600/101; 604/164, 604/264; 606/1, 167, 184, 185

[56] References Cited

U.S. PATENT DOCUMENTS

| | | |
|---|---|---|
| 207,932 | 9/1878 | Alvord. |
| 1,147,408 | 7/1915 | Kells. |
| 2,699,770 | 1/1955 | Fourestier et al.. |
| 2,932,294 | 4/1960 | Fourestier et al.. |
| 3,224,320 | 12/1965 | Knudsen. |
| 3,437,747 | 4/1969 | Sheldon. |
| 3,459,189 | 8/1969 | Alley et al.. |
| 3,556,085 | 1/1971 | Takahashi. |
| 3,653,388 | 4/1972 | Tenckhoff. |
| 3,822,697 | 7/1974 | Komiya. |
| 3,870,036 | 3/1975 | Fiore. |
| 3,961,621 | 6/1976 | Northeved. |
| 4,112,932 | 9/1978 | Chiulli. |
| 4,191,191 | 3/1980 | Auburn. |
| 4,222,375 | 9/1980 | Martinez. |
| 4,248,214 | 2/1981 | Hannah et al.. |
| 4,254,762 | 3/1981 | Yoon. |
| 4,269,192 | 5/1981 | Matsuo. |

(List continued on next page.)

FOREIGN PATENT DOCUMENTS

| | | |
|---|---|---|
| 0135364 | 3/1985 | European Pat. Off.. |
| 0265193 | 4/1988 | European Pat. Off.. |
| 0312787 | 4/1989 | European Pat. Off.. |
| 0347140 | 12/1989 | European Pat. Off.. |
| 0369936 | 5/1990 | European Pat. Off.. |
| 0369937 | 5/1990 | European Pat. Off.. |
| 0497347 | 5/1992 | European Pat. Off.. |
| 0604197 | 6/1994 | European Pat. Off.. |
| 1370580 | 1/1965 | France. |
| 2218901 | 10/1973 | Germany. |
| 2538758 | 3/1977 | Germany. |
| 2929233 | 1/1980 | Germany. |
| 2922239 | 12/1980 | Germany. |
| 4020956 | 1/1991 | Germany. |
| 9112976 | 2/1992 | Germany. |
| 4133073 | 4/1992 | Germany. |
| 4116648 | 11/1992 | Germany. |
| 9215725 | 1/1993 | Germany. |
| 568666A | 3/1993 | Japan. |
| 942730 | 7/1982 | U.S.S.R.. |
| 1329769 | 8/1987 | U.S.S.R.. |

OTHER PUBLICATIONS

Liese, G. J., et al. "Fiber–Optic Stylet for Needle Tip Localisation", *Applied Optics*, Oct. 01, 1985, vol. 24, No. 19, pp. 3125–3126, Fig. 1.

*Primary Examiner*—Glenn K. Dawson
*Attorney, Agent, or Firm*—Rodman & Rodman

[57] ABSTRACT

A new and improved laparoscopic trocar and sleeve assembly in which the trocar is provided with a transparent tip and accommodates a light telescope for supplying a video console, so that while the trocar is being surgically inserted through the abdominal wall and into the abdominal cavity, visualization on the video console will be possible to avoid injury to blood vessels in the abdominal cavity wall or injury to any of the internal organs located in the abdominal cavity. Once clear visualization is established, conventional laparoscopic procedures can be carried out safely.

29 Claims, 5 Drawing Sheets

U.S. PATENT DOCUMENTS

| | | |
|---|---|---|
| 4,299,230 | 11/1981 | Kubota . |
| 4,311,138 | 1/1982 | Sugarman . |
| 4,319,563 | 3/1982 | Kubota . |
| 4,356,826 | 11/1982 | Kubota . |
| 4,498,902 | 2/1985 | Ash et al. . |
| 4,535,773 | 8/1985 | Yoon . |
| 4,537,593 | 8/1985 | Alchas . |
| 4,567,882 | 2/1986 | Heller . |
| 4,601,710 | 7/1986 | Moll . |
| 4,895,431 | 1/1990 | Tsujiuchi et al. . |
| 4,901,142 | 2/1990 | Ikuno et al. . |
| 5,066,288 | 11/1991 | Deniega et al. . |
| 5,089,000 | 2/1992 | Agee et al. . |
| 5,098,388 | 3/1992 | Kulkashi et al. . |
| 5,147,376 | 9/1992 | Pianetti . |
| 5,159,920 | 11/1992 | Condon et al. . |
| 5,163,941 | 11/1992 | Garth et al. . |
| 5,207,647 | 5/1993 | Phelps . |
| 5,246,425 | 9/1993 | Hunsberger et al. . |
| 5,250,068 | 10/1993 | Ideguchi et al. . |
| 5,256,149 | 10/1993 | Banik et al. . |
| 5,269,316 | 12/1993 | Spitalny . |
| 5,271,380 | 12/1993 | Riek et al. . |
| 5,290,276 | 3/1994 | Sewell, Jr. . |
| 5,385,572 | 1/1995 | Nobles et al. ............ 606/185 |
| 5,431,151 | 7/1995 | Riek et al. . |
| 5,569,160 | 10/1996 | Sauer et al. ............ 606/185 |

VISUALLY DIRECTED TROCAR AND METHOD

TECHNICAL FIELD

This invention relates to the field of operative and diagnostic laparoscopic surgical procedures and in particular to a new and improved visually directed trocar laparoscopic instrument and method of use for conducting such procedures.

BACKGROUND OF THE INVENTION

Operative and diagnostic laparoscopy is the most commonly performed surgical procedure in the United States today. Therefore, any complication associated with this procedure poses a major public health concern.

Conventional known laparoscopic procedures usually are carried out as follows:

1. An instrument known as the Veress needle is blindly inserted through the navel into the abdominal cavity of a patient.
2. Carbon dioxide is delivered blindly through the Veress needle into the abdomen.
3. A laparoscopy trocar assembly comprised by a trocar and trocar sleeve is blindly inserted through the navel into and through the abdominal wall of the abdominal cavity.
4. The trocar is withdrawn from the trocar sleeve and a light telescope with light source placed in the sleeve thus making visualization of the interior of the cavity possible.
5. Once clear visualization is established a variety of surgical procedures can be carried out safely through the central opening in the trocar sleeve with remotely operable surgical instruments in a conventional known manner.

There are several reports in the medical literature that the first two steps of a laparoscopic procedure as outlined above can be omitted, and the laparoscopic trocar assembly be directly inserted blindly into the abdominal cavity. Results of these papers indicate that complications can still be expected since the entry through the abdominal cavity wall into the abdominal cavity remains blind.

SUMMARY OF THE INVENTION

It is therefore a primary purpose of this invention to make available a new and improved, visually directed, laparoscopic instrument which allows the laparoscopic surgeon to enter the abdominal or other cavity of a patient under direct vision. This visually directed laparoscopic procedure will eliminate most if not all major and minor complications associated with the blind invasive surgical technique presently employed in laparoscopic procedures as described above.

In practicing the invention a new and improved laparoscopic instrument is provided with an elongated, hollow trocar having a tipped end suitable for insertion through layers of human skin and flesh forming the walls of a cavity with the tipped end being fabricated from light transparent material. The tipped end of light transparent material preferably is shaped to form a light transmission and imaging element for projecting light outwardly into an abdominal or other cavity of a patient, and for receiving back and directing light images onto a suitable light image receptor of a conventional miniaturized light telescope designed for surgical purposes. The tipped end of light transparent material is formed to pierce human flesh. In other embodiments, a cutting member which can be formed of metal or ceramic for example, is adapted to cooperate with the tipped end of light transparent material to provide the tipped end with a cutting edge for piercing human flesh to permit surgical insertion of the tipped end through human flesh and into a body cavity.

The hollow trocar has a central passageway formed therein of sufficient diameter to accommodate the elements of a miniaturized light telescope together with essential power supply conductors for energizing the light source and light receptors such as a bundle of fiber optic light coupling elements for deriving and providing back light images usable for laparoscopic diagnostic procedures even while the trocar is being surgically inserted through the navel and is penetrating through the layers of skin and abdominal wall of a patient and on into the abdominal cavity.

In preferred embodiments of the invention, the laparoscopic instrument includes a hollow tubular trocar sleeve that surrounds and encloses the trocar for a substantial portion of its length to form a combined trocar and sleeve assembly. The trocar is slidable lengthwise relative to the trocar sleeve whereby the trocar can be removed after visually controlled physical placement of the trocar and sleeve assembly into the abdominal wall of a patient's abdominal cavity at a desired location and to a desired depth. The trocar then can be replaced with a somewhat large fiber optic light telescope and video imaging system, and other remotely manipulatable surgical instrument inserted through the central opening of the trocar sleeve in a conventional known manner.

The invention makes available a new and improved laparoscopic procedure comprising mounting a miniaturized light telescope with light source together with suitable miniaturized power supply conductors, and fiber optic coupling and light receptor elements in the hollow trocar prior to starting the laparoscopic procedure. The light telescope then is energized from an electric power source and the output of the light receptors supplied to a video display. Following this setup, the tipped and lighted end of the trocar with or without the cutting member is placed at a point, such as the navel, on a patient's abdomen to be penetrated while observing such placement on the video display. The cutting member may appear as a line or narrow band on the video display and does not obscure vision through the light transparent material. The lighted trocar then is surgically inserted by being pressed slowly and carefully into and through the walls of the patient's abdomen while observing the progress of the trocar assembly as it travels into and through the wall of the abdominal or other cavity. During this process, the operator, by properly controlling orientation and progress of the trocar tip, can assure that the trocar does not penetrate into the abdominal cavity at a place or for a distance where it might injure any blood vessels within the abdominal cavity walls or internal organs within the abdominal cavity. A handle provided on the trocar facilitates manipulation and control of the trocar tip penetration.

BRIEF DESCRIPTION OF DRAWINGS

These and other objects, features and many of the attendant advantages of this invention will be appreciated more readily as the same becomes better understood from a reading of the following detailed description, when considered in connection with the accompanying drawings, wherein like parts in each of the several figures are identified by the same reference characters, and wherein.

BEST MODE OF PRACTICING THE INVENTION

Figure 1:
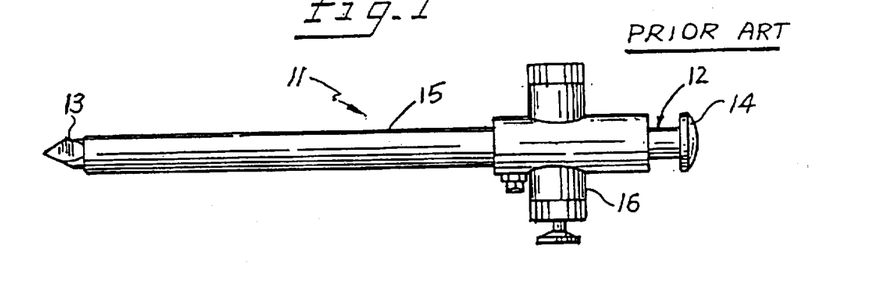
FIG. 1 is a side elevational view of a know, combined trocar and sleeve assembly with trumpet valve and stopcock components constructed according to the prior art.
Figure 2:
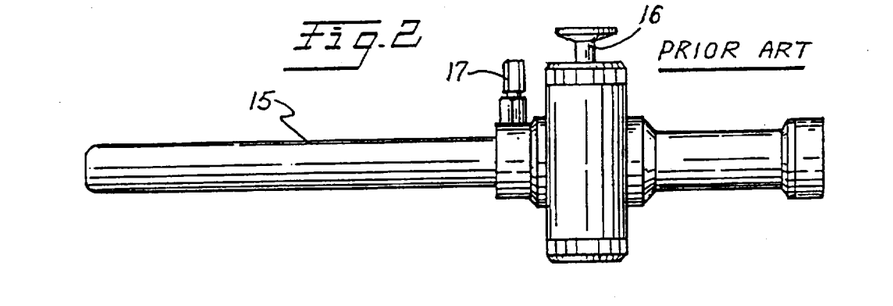
FIG. 2 is a side elevational view of a known trocar sleeve having a different trumpet valve construction from the assembly shown in FIG. 1 and built according to the prior art.
Figure 3:
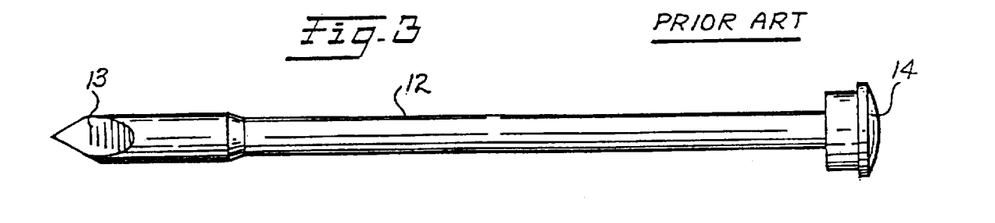
FIG. 3 is a side elevational view of a known trocar design suitable for use with the sleeve shown in FIG. 2 and built according to the prior art.

As noted earlier in the brief description of the drawings, FIGS. 1, 2 and 3 of the drawings illustrate a prior art, known trocar and sleeve assembly now being used by the medical profession in performing laparoscopic procedures such as laparoscopic cholecystectomies. Other similar laparoscopic procedures can be performed using the instrument. In these drawings, FIG. 1 is an elevational side view of a known combined trocar and trocar sleeve assembly 11 comprised by an elongated, solid, stainless steel trocar 12, best seen in FIG. 3, and a hollow, tubular trocar sleeve 15 shown in FIG. 2. Trocar 12 includes a pointed tipped end 13, which may be either pyramidal or the like or conical in configuration, and is sufficiently sharp to be able to penetrate and be physically pressed through the navel, layers of skin and abdominal walls of a patient in order to provide access to the interior of the abdominal cavity. Trocar 12 is a solid rod of appropriate diameter, for example of from 6 to 9 millimeters in diameter, and terminates in a push cap 14 that facilitates surgical insertion of the stiff elongated rod 12 into and through the navel of a patient by pushing on cap 14.

The trocar 12 is physically supported within the trocar sleeve 15 shown in FIG. 2 of the drawings. Trocar sleeve 15 is a cylindrical hollow tube fabricated from biologically compatible material, such as stainless steel. Sleeve 15 has a central opening into which the trocar 12 fits in a relatively tight manner, but is sufficiently loose to allow trocar 12 to be slid lengthwise relative to the sleeve 15 and withdrawn. Trocar sleeve 15 in most applications also includes at least one trumpet valve 16 as shown in both FIGS. 1 and 2 as well as one or more insufflation stopcocks shown at 17 in FIG. 2. These elements all are of known construction and operation and need not be described in detail with respect to the present invention. In use the assembled trocar and sleeve appear as shown at 11 in FIG. 1 of the drawings.

As described earlier in the specification, conventional laparoscopic procedure is carried out by first blindly inserting a Veress (not shown) through the navel into the abdominal cavity of the patient. Carbon dioxide gas then is delivered blindly through the Veress needle into the abdomen in an effort to draw the skin of the abdomen on which the navel is disposed away from any organs resting internally within the abdominal cavity and to improve visualization within the cavity. It is at this point that the laparoscopic trocar and sleeve assembly 11 is blindly inserted through the navel into the abdominal cavity.

After insertion of the trocar and sleeve assembly 11, the trocar 12 is withdrawn from the trocar sleeve 15 leaving the sleeve with its appended elements such as the trumpet valve 16 and insufflation stopcock 17 extending into the abdominal cavity. A light telescope with a miniaturized light source of conventional commercially available construction is inserted through the central opening of the trocar sleeve 15 to establish visualization of the intra-abdominal organs. Once clear visualization is established, a variety of surgical procedures can be carried out safely through the use of remotely operable surgical instruments inserted into the interior of the abdominal cavity through the central passageway in the trocar sleeve 15 in a known manner. Upon completion of the procedures, all instruments including the light telescope are withdrawn along with the trocar sleeve and the opening through which they were inserted is sewn up.

It is believed apparent that the step of introducing the trocar and sleeve assembly into the abdominal cavity using conventional known techniques, is a blind procedure and frequently causes injury to blood vessels in the walls of the abdominal cavity and organs located within the abdominal cavity close to the point of entry.

Figure 4:
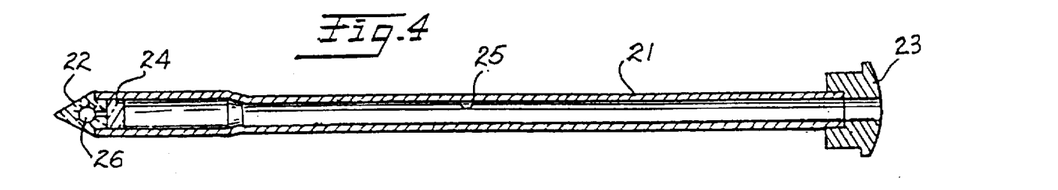
FIG. 4 is a longitudinal sectional view of a new and improved trocar having a transparent tipped end constructed according to the invention.
Figure 5:
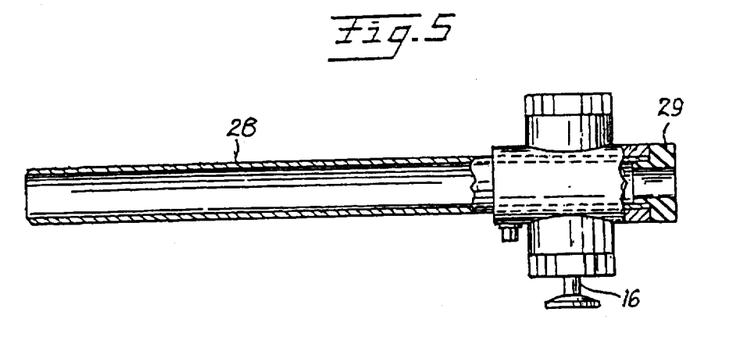
FIG. 5 is a longitudinal view of a hollow trocar sleeve suitable for use with the new and improved trocar shown in FIG. 4.
Figure 6:
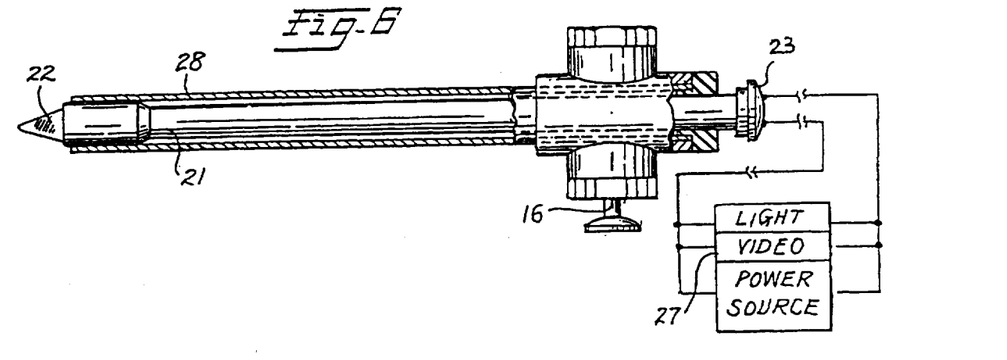
FIG. 6 is a longitudinal sectional view of a new and improved combined hollow trocar and sleeve assembly employing the elements of FIGS. 4 and 5, and constructed in accordance with the invention.

In order to avoid possible injury to the blood vessels and/or internal organs, the present invention was devised and is illustrated in FIG. 4, FIG. 5 and FIG. 6 of the drawings together with FIGS. 7 through FIG. 15 which show alternative constructions of the trocar according to the invention.

Figure 7:
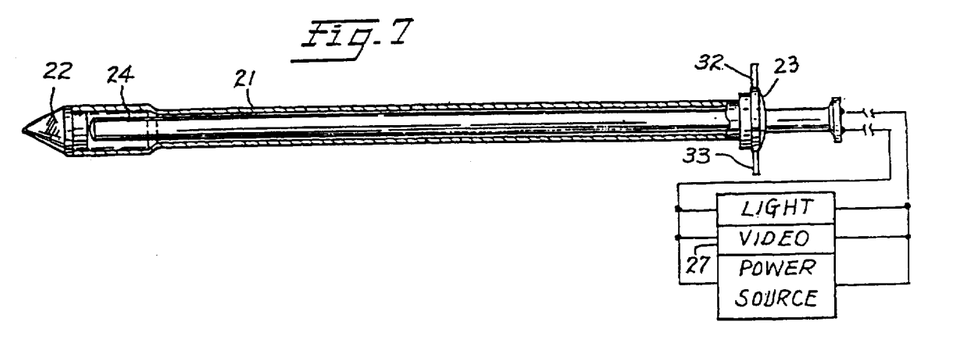
FIG. 7 is a longitudinal sectional view of an alternative form of a new and improved hollow trocar having extra exterior handles constructed according to the invention.

FIG. 4 is a longitudinal sectional view taken along the longitudinal axis of an elongated, cylindrically-shaped trocar having a hollow tubular body 21 fabricated from an inflexible material (such as stainless steel) that is compatible with human flesh. Trocar 21 has a tipped end 22 that is sufficiently sharp that it can be surgically inserted through layers of skin and human flesh by physically pressing on a push cap 23 secured to the opposite end of the trocar. Tipped end 22 is fabricated from light transparent material such as glass or a space-age plastic and is shaped to form a light transmission and imaging element for projecting light outwardly into an abdominal or other cavity of a patient and for directing light images received back onto a suitable light image receptor 24. Tipped end, 22 also has a substantially solid piercing point, as shown in FIG. 4, which can be of pyramidal or the like or conical configuration. As shown in FIGS. 4 and 7, for example, a tapered portion of the tipped end 22 projects from the tubular body 21 and a non-tapered portion of the tipped end 22 is recessed in the tubular body 21.

Light image receptor 24 is part of a commercially available, miniaturized, medical light telescope for surgical use and is not part of this invention. Receptor 24 may comprise a plurality of light receiving input ends of a bundle of fiber optic light coupling elements (not shown) or alternatively a semiconductor light to electric signal transducer. Trocar 21 has a central opening 25 which is of sufficient diameter to accommodate passage of the elements of the miniaturized light telescope such as a light source 26 comprised by a bundle of fiber optic elements, a semiconductor laser or a light bulb together with essential power supply conductors and/or fiber optic light coupling elements (not shown). These elements serve to energize light source 26 and light receptors 24 (or transducers if required) together with fiber optical or electric signal coupling elements for deriving and supplying video signals to a video camera 27, comprising a part of the light telescope system. The video camera 27 excites a suitable video monitor (not shown) for producing video images usable for diagnostic and surgical purposes even while the trocar is being surgically inserted into and is penetrating the layers of skin on the navel prior to proceeding into the abdominal cavity.

Trocar 21 shown in FIG. 4 is designed for use with a trocar sleeve 28 shown in FIG. 5. Trocar sleeve 28 comprises an elongated hollow tubular body of stainless steel or other similar material having an open end through which the tipped transparent end 22 of trocar 21 projects and a, rubber sealing cap 29 on the opposite end. Preferably a trumpet valve 16 and insufflation stopcock, such as 17 shown in FIG. 2, are included on the hollow trocar sleeve 28. If desired, the trocar sleeve 15 shown in FIG. 2 and trocar sleeve 28 in FIG. 5 can be made to be interchangeable.

Trocar sleeve 28 is designed to physically surround and enclose trocar 21 for a substantial portion of its length to form a combined trocar and sleeve assembly shown in FIG. 6 of the drawings. The trocar 21 is slidable lengthwise relative to trocar sleeve 28 so that the trocar can be removed after visual surgical insertion of the trocar 21 and sleeve 28 assembly into the abdominal cavity of a patient at a desired location and to a desired depth. After removal of trocar 21, it is replaced with a suitable known fiber optic light source and video imaging system (not shown) and supplemented with other remotely manipulatable surgical instruments (not shown) which can be inserted through the central opening of the trocar sleeve 28 in a conventional, known manner.

FIG. 7 illustrates an alternative design of the trocar 21 wherein suitable handles shown at 32 and 33 are provided on opposite sides of the elongated tubular body of the trocar 21 at the end opposite transparent tip end 22. In all other respects, the trocar of FIG. 7 is similar to that described with relation to FIG. 4. Surgical insertion of the trocar 21 of FIG. 7 and trocar sleeve 28 in assembled relation as depicted by FIG 6, through the navel of a patient can be better accomplished and more easily guided using the handles 32 and 33 while visually observing the progress of the trocar through the layers of skin and abdominal walls of a patient. By observing the pre-imminent entry of the trocar assembly into the abdominal cavity under conditions where the position of blood vessels in the walls of the abdominal cavity and internal organs located within the abdominal cavity can be observed, prior to thrusting the trocar all the way into the cavity, injury to the blood vessels and internal organs can be avoided.

Figures 8A, 8B:
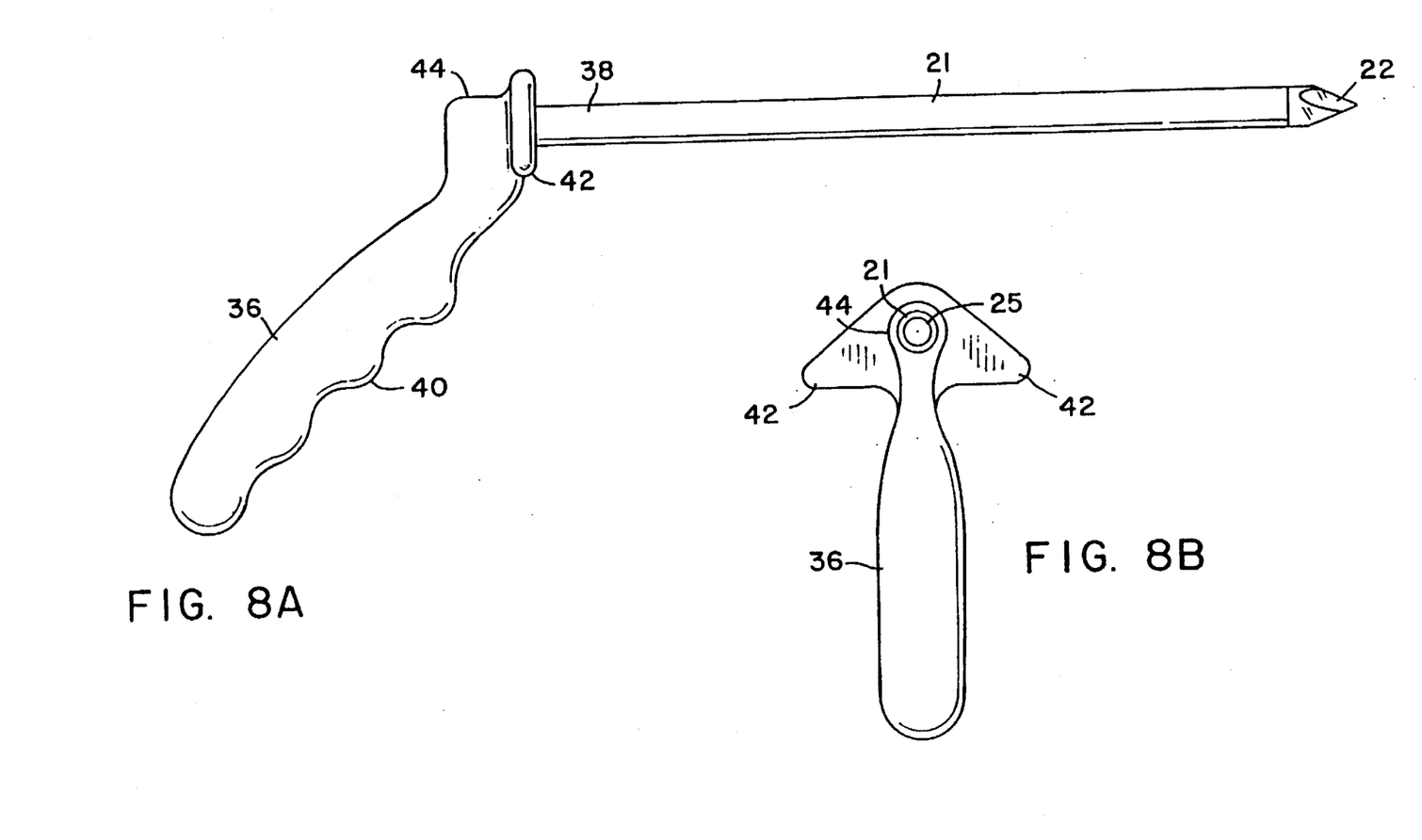
FIG. 8A is a side elevational view of another embodiment of a new and improved hollow trocar with an alternative form of handle, the opposite side of the handle being symmetrical to the side shown.
FIG. 8B is an end view of FIG. 8A as taken from the handle end of FIG. 8A.

FIGS. 8A and 8B illustrate another alternative design of the trocar 21. A handle 36, preferably formed of plastic, is affixed at or proximate an end 38 of the trocar 21, opposite the tipped end 22. As shown in FIG. 8A, the handle 36 extends away from the trocar 21 so as to avoid interference with the central opening 25 at the trocar end 38. The handle 36 includes a finger contour portion 40 to accommodate the individual fingers and is sufficiently elongated to permit gripping by all of the fingers. A thumb flange 42 is provided on each side of the handle 36 for right or left handed users to rest their thumb during exertion of manual pressure on the trocar 21 in the direction of the tipped end 22. The handle 36 further includes a mounting portion 44 adjacent the thumb flange 42 which encircles the trocar at the end 38 and can be bonded or otherwise secured to the trocar end 38.

Figure 9:
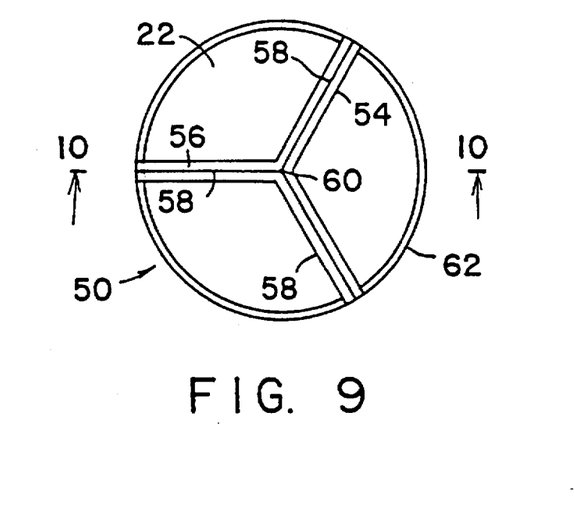
FIG. 9 is an end view of the tipped end of the new and improved hollow trocar showing an alternative form of the tipped end.
Figure 11:
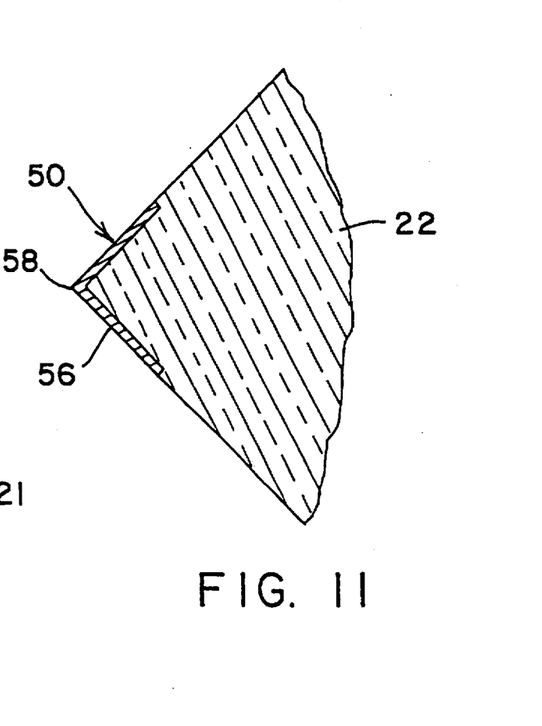
FIG. 11 is an enlarged detail section taken on the line 11—11 of FIG. 10.

FIG. 9 illustrates an alternative design of the tipped end 22 as used on the trocar 21. The tipped end 22, which is shown for example as a three-sided pyramidal tip, is combined with a cutter member 50. The cutter member 50, which can be formed of a suitable hardened material such as stainless steel or ceramic for example, includes V-shaped (in cross-section) cutting portions 52, 54 and 56 that wrap onto the pyramidal corners of the tipped end 22 as shown in FIG. 11. Each of the cutting portions 52, 54 and 56 have sharp edges that converge to a common sharp point 60 as shown in FIG. 9. An annular reinforcing ring 62 joins the cutting portions 52, 54 and 56.

The cutting member 50 can be formed as a separate member and placed as an insert in a mold for molding the tipped end 22 from plastic. Alternatively the cutting member 50 and the tipped end 22 can be separately formed and bonded together with a suitable know medical grade adhesive.

The cutting member 50 can also be modified to include four cutting portions for incorporation in a tipped end 22 of a four-sided pyramidal configuration. In addition, the cutting member 50 can be incorporated in a tipped end 22 of conical configuration, wherein the cutting edges 58 project slightly from the curved conical surface.

Figure 12:
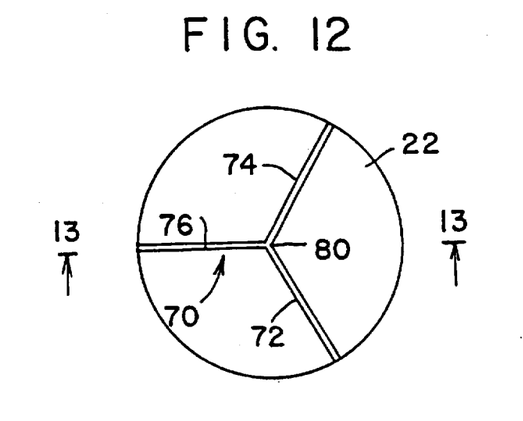
FIG. 12 is an end view of the tipped end of the new and improved hollow trocar showing a further alternative form of the tipped end.
Figure 13:
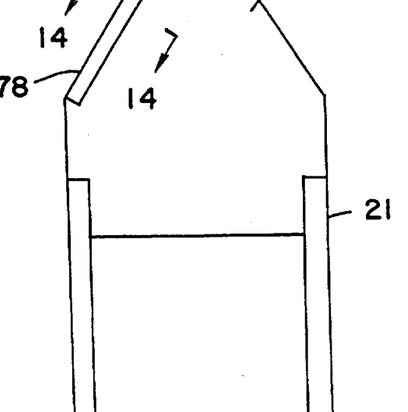
FIG. 13 is a fragmentary sectional view taken on the line 13—13 of FIG. 12.
Figure 14:
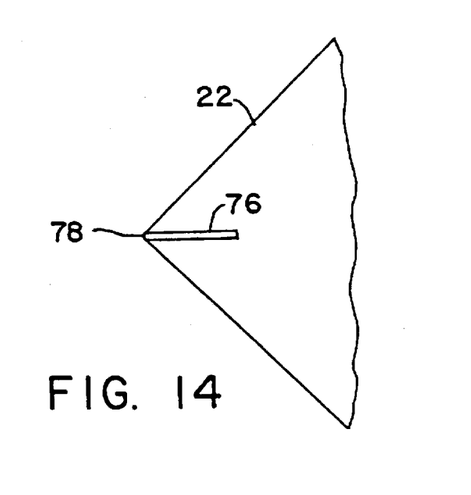
FIG. 14 is one version of an enlarged detail section taken on the line 14—14 of FIG. 13.

FIG. 12 illustrates a further alternative design of the tipped end 22 as used on the trocar 21. The tipped end 22, which is shown for example as a three-sided pyramidal tip, is combined with a cutter member 70. The cutter member 70, which can be formed of stainless steel or ceramic for example, includes bar-like cutting portions 72, 74 and 76 that are partly disposed within the tipped end 22 in alignment with the pyramidal corners of the tipped end as shown in FIG. 14. Each of the cutting portions 72, 74 and 76 have sharp edges 78 that converge to a common sharp point 80 as shown in FIG. 12.

Figure 15:
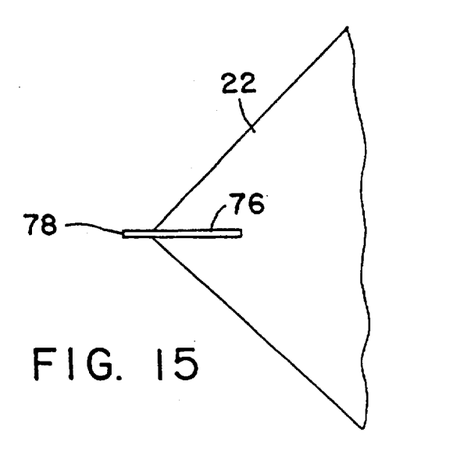
FIG. 15 is another version of an enlarged detail section taken on the line 14—14 of FIG. 13.

The cutting portions 72, 74 and 76 can be imbedded in the tipped end 22 up to the sharp edge 78 as shown in FIG. 14 or the sharp edge 78 can project slightly as shown in FIG. 15.

The cutting member 70 can also be modified to include four cutting portions for incorporation in a tipped end 22 of four-sided pyramidal configuration. In addition, the cutting member 70 can be incorporated in a tipped end of conical configuration in the arrangement such as shown in FIGS. 14 or 15.

Figure 10:
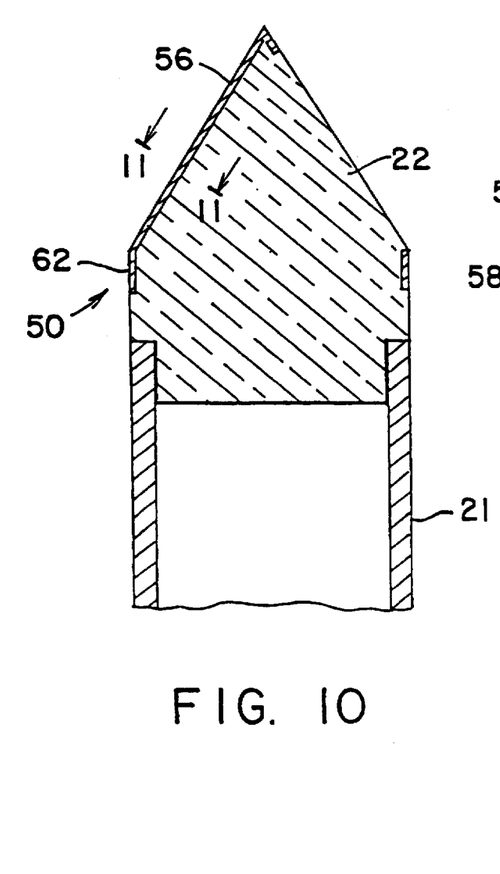
FIG. 10 is a fragmentary sectional view taken on the line 10—10 of FIG. 9.

Molding of a tipped end 22 with the cutting member 70 is in accordance with the manner previously described for the tipped end 22 of FIGS. 9–11.

If desired, the conical tipped end 22 can include a cutting member 50 or 70 that has a single cutting portion extending across opposite sides of the conical tipped end.

Also, if desired, the cutting members 50 and 70 need not extend to the pointed extremity of the tipped end 22, thereby enabling the pointed extremity of the tipped end 22 to pass light.

In conducting a laparoscopic procedure employing the novel, hollow, laparoscopic trocar 21 with a tipped end 22 fabricated from light transparent material shaped to form a light transmission and receiving element with or without a cutting member, the procedure is commenced by activating the miniaturized light telescope including the light source and suitable miniaturized light receptors, power supply conductors and fiber optic couplings provided in the assembled hollow trocar and sleeve, while using the trocar of any of FIGS. 4–15, prior to starting the procedure. After the light source is activated, any output from the light receptors 24 is supplied to a video display console (not shown) via video receiver 27. The tipped and lighted end of the trocar 21 then is placed at the point on the patient's abdomen (such as the navel) to be penetrated while observing such placement on the video display. The trocar and sleeve assembly then is pushed slowly into and through the layers of skin and support flesh of the patient's navel while observing the progress of the trocar assembly on the video display while it travels into and through the navel.

In using the trocar with the cutting members 50 or 70, the cutting edges appear as lines or narrow bands and do not obscure vision through the light telescope and do not obscure the video display. During the insertion process, the positioning of the trocar can be adjusted by the laparoscopic surgeon, if necessary, by manipulation of the push cap 23 and/or side handles 32 and 33, or the handle 36, to assure that the trocar does not penetrate into the abdominal cavity at a place or for a distance where it might penetrate and injure blood vessels in the walls of the cavity or internal organs within the abdominal cavity.

In the above recited procedure, the combined assembly of trocar 21 and trocar sleeve 28 are inserted together with the light source and video display components of the miniaturized light telescope contained therein. After completing the visually directed insertion of the combined trocar and sleeve assembly as described above, the trocar 21 together with its light source and video display components is removed from sleeve 28 which remains implanted in the abdominal cavity. The trocar 21 then is replaced in implanted sleeve 28 with the fiber optic light source and video imaging system of the miniaturized light telescope along with any other assorted remotely manipulatable surgical instruments, as needed, which are inserted through the central opening in the trocar sleeve in a conventional known manner.

PRACTICAL APPLICABILITY

This invention provides to the medical profession a new laparoscopic instrument which allows the laparoscopic surgeon to enter the abdominal cavity of a patient under conditions where he can directly, visually follow the progress of the pointed tip of the instrument as it passes through the layers of skin and supporting walls of the abdominal cavity. Hence, prior to entering the abdominal cavity to any great depth, the surgeon can observe whether there are any blood vessels in the supporting walls or internal organs which would be punctured or otherwise damaged if the trocar is allowed to penetrate too deeply at a selected point. The new procedure and instrument will eliminate many major and minor complications associated with the prior known blind invasive laparoscopic surgical techniques employed to implant the laparoscopic trocar and sleeve assembly into the abdominal cavity.

Having described several embodiments of a new and improved laparoscopic instrument and procedure according to the invention, it is believed obvious that other modifications and variations of the invention will be suggested to those skilled in the art in the light of the above teachings. It is therefore to be understood that changes may be made in the particular embodiments of the invention described which are within the full intended scope of the invention as defined by the appended claims.

What is claimed is:

1. A surgical penetration device comprising:
   a) an inflexible elongated member having a first end,
   b) a light transmission and imaging member formed essentially of transparent material, provided at the first end of said elongated member to form an extension of said elongated member and project light and receive light images,
   c) cutting means including a cutting member at said first end cooperable with said light transmission and imaging member to provide said light transmission and imaging member with a cutting edge for piercing human flesh to permit surgical insertion of said light transmission and imaging member through human flesh into a body cavity, and
   d) said elongated member having means for containing a conventional lighting means and a conventional light image receiving means in the form of a conventional telescope to cooperate with said light transmission and imaging member, said containing means being sized to permit detachable slidable insertion of the conventional telescope in the elongated member and slidable removal of the conventional telescope from the elongated member.

2. The surgical penetration device as claimed in claim 1 wherein said light transmission and imaging member has an outside surface and said cutting member is joined to the outside surface of said light transmission and imaging member.

3. The surgical penetration device as claimed in claim 1 wherein said light transmission and imaging member has an outside surface and said cutting member is adapted to extend beyond said outside surface to pierce human flesh and permit surgical insertion of said light transmission and imaging member through human flesh.

4. The surgical penetration device as claimed in claim 3 wherein said cutting member includes a blade edge projecting from said light transmission and imaging member.

5. The surgical penetration device as claimed in claim 1 wherein said cutting member includes a plurality of blade edges in intersecting planes.

6. The surgical penetration device as claimed in claim 1 wherein said light transmission and imaging member is formed of plastic and said cutting member is incorporated in said light transmission and imaging member.

7. The surgical penetration device as claimed in claim 6 wherein said cutting member includes a plurality of blade edges in intersecting planes projecting away from said light transmission and imaging member.

8. The surgical penetration device as claimed in claim 1 wherein said light transmission and imaging member has a sharp pointed tip.

9. The surgical penetration device as claimed in claim 1 wherein said light transmission and imaging member is affixed to said first end of said inflexible elongated member.

10. The surgical penetration device as claimed in claim 9 wherein said elongated member is hollow.

11. The surgical penetration device as claimed in claim 9 wherein said elongated member is a cylinder.

12. The surgical penetration device as claimed in claim 1 wherein said light transmission and imaging member has a light transmissible tapered section and a light transmissible nontapered section, a predetermined amount of said nontapered section being recessed in the first end of said elongated member.

13. The surgical penetration device as claimed in claim 12 wherein the nontapered section of said light transmission and imaging member is substantially circular in cross section.

14. The surgical penetration device as claimed in claim 12 wherein the predetermined amount of said nontapered section is integrally joined to said elongated member at said first end of said elongated member.

15. The surgical penetration device as claimed in claim 1 wherein said light transmission and imaging member is formed of glass.

16. The surgical penetration device as claimed in claim 1 wherein said light transmission and imaging member is formed of plastic.

17. The surgical penetration device as claimed in claim 1 wherein said elongated member has a second end opposite said first end, and a handle member being provided proximate said second end to facilitate manipulation of said elongated member.

18. The surgical penetration device as claimed in claim 1 including handle means joined to said elongated member to permit one-handed manipulation of said elongated member and to permit the same one hand to simultaneously exert manual pressure on said elongated member in the direction of said light transmission and imaging member for surgical insertion of said light transmission and imaging member through human flesh into a body cavity.

19. The surgical penetration device as claimed in claim 18, said handle means extending away from the elongated member to avoid interference with said means for containing the conventional lighting means and the conventional light image receiving means.

20. The surgical penetration device as claimed in claim 18 wherein said handle means has a thumb rest for the right and left hands to permit use of said handle means with either hand.

21. The surgical penetration device as claimed in claim 18 wherein said handle means is sufficiently elongated to permit gripping by all of the fingers of the one hand.

22. The surgical penetration device as claimed in claim 1 wherein said inflexible elongated member is tubular with a hollow space, said hollow space in said inflexible elongated member extending to said light transmission and imaging member, and said hollow space constituting the containing means for containing the conventional lighting means and the conventional light image receiving means in the form of a conventional telescope.

23. The surgical penetration device as claimed in claim 1 wherein the light transmission and imaging member forms a closure at the first end of said inflexible elongated member.

24. A method of visualizing insertion of a surgical device through flesh into a body cavity comprising the steps of:

a) providing a hollow trocar with a tubular body and a light transmission and imaging member with a cutting member for piercing human flesh for surgical insertion of the light transmission and imaging member through human flesh, b) joining said light transmission and imaging member to one end of said tubular body formed of a biocompatible material, c) slideably locating a conventional lighting means and a conventional light image receiving means in the form of a conventional light telescope in said hollow trocar proximate said light transmission and imaging member to enable light from the lighting means to project outwardly away from said light transmission and imaging member and to permit the light image receiving means to receive light images that pass from outside said light transmission and imaging member through said light transmission and imaging member while said light transmission and imaging member is being inserted through the flesh into a body cavity, whereby said light transmission and imaging member provides a receivable image of the flesh and body cavity being entered, and d) keeping the conventional light telescope in the hollow trocar in a manner that permits slideable removal of the conventional light telescope from the hollow trocar when the hollow trocar is removed from the flesh.

25. The method of claim 24 including slidably locating said hollow trocar with said light transmission and imaging member in a sleeve and fixing the position of said hollow trocar relative to the sleeve such that substantially only the light transmission and imaging member with the cutting member projects from one end of the sleeve to permit insertion of the sleeve with the light transmission and imaging member through the flesh into a body cavity.

26. The method of claim 24 including monitoring the light images received by the light image receiving means on a video screen while the light transmission and imaging member is being inserted through the flesh into a body cavity to obtain continuous video aided visual imaging of the internal location of the light transmission and imaging member during such insertion.

27. The method of claim 26 including slidably removing the hollow trocar with the conventional light telescope from said sleeve, while said sleeve remains inserted through the flesh into a body cavity.

28. The method of claim 27 including reinserting the conventional light telescope in the sleeve, without the hollow trocar.

29. The method of claim 24 including joining a handle member to the tubular body proximate an opposite end of the tubular body to manipulate said trocar and to exert manual pressure on said trocar in the direction of said light transmission and imaging member for surgical insertion of said light transmission and imaging member through human flesh into a body cavity.

* * * * *